(12) United States Patent
Rezai et al.

(10) Patent No.: US 8,612,005 B2
(45) Date of Patent: Dec. 17, 2013

(54) NEUROSTIMULATION FOR AFFECTING SLEEP DISORDERS

(75) Inventors: Ali Rezai, Bratenhal, OH (US); Jorge Alvaro Gonzalez-Martinez, Cleveland Heights, OH (US); Ashwini Sharan, Mt. Laurel, NJ (US)

(73) Assignee: The Cleveland Clinic Foundation, Cleveland, OH (US)

( * ) Notice: Subject to any disclaimer, the term of this patent is extended or adjusted under 35 U.S.C. 154(b) by 2012 days.

(21) Appl. No.: 10/502,820

(22) PCT Filed: Jan. 31, 2003

(86) PCT No.: PCT/US03/02860
§ 371 (c)(1),
(2), (4) Date: Apr. 12, 2005

(87) PCT Pub. No.: WO03/072186
PCT Pub. Date: Sep. 4, 2003

(65) Prior Publication Data
US 2005/0177192 A1    Aug. 11, 2005

Related U.S. Application Data

(60) Provisional application No. 60/353,697, filed on Feb. 1, 2002.

(51) Int. Cl.
*A61N 1/36*    (2006.01)

(52) U.S. Cl.
USPC ............................................. 607/45; 607/46

(58) Field of Classification Search
USPC ................. 607/1, 2, 45, 46; 600/544, 545
See application file for complete search history.

(56) References Cited

U.S. PATENT DOCUMENTS

| | | | |
|---|---|---|---|
| 3,762,396 A | 10/1973 | Ballentine et al. | |
| 4,572,165 A * | 2/1986 | Dodier | 607/82 |
| 5,105,354 A * | 4/1992 | Nishimura | 600/484 |
| 5,335,657 A * | 8/1994 | Terry et al. | 607/45 |
| 5,676,655 A | 10/1997 | Howard et al. | |
| 6,128,537 A * | 10/2000 | Rise | 607/45 |
| 6,194,437 B1 | 2/2001 | Horwell et al. | |
| 6,356,784 B1 * | 3/2002 | Lozano et al. | 607/2 |
| 6,368,331 B1 | 4/2002 | Front et al. | |
| 6,760,626 B1 * | 7/2004 | Boveja | 607/45 |
| 2002/0032375 A1 | 3/2002 | Bauch et al. | |
| 2002/0116042 A1 * | 8/2002 | Boling | 607/122 |
| 2002/0183607 A1 | 12/2002 | Bauch et al. | |
| 2003/0009207 A1 * | 1/2003 | Paspa et al. | 607/116 |

OTHER PUBLICATIONS

U.S. Appl. No. 60/353,695, filed Feb. 2, 2002, Rezi et al.

(Continued)

*Primary Examiner* — Joseph Dietrich
(74) *Attorney, Agent, or Firm* — Tarolli, Sundheim, Covell & Tummino LLP (57) ABSTRACT

A method of affecting a sleep disorder in a subject having the sleep disorder and a method of affecting a normal awakeness-sleep cycle in a subject having an abnormal awakeness-sleep cycle, said methods comprising: a) identifying at least one nucleus in a brain of the subject, said nucleus being a nucleus of the sleep circuitry of the brain; and b) stimulating the at least one identified nucleus so as to modulate the nucleus, thereby affecting the sleep disorder.

55 Claims, 2 Drawing Sheets

(56) References Cited

OTHER PUBLICATIONS

Jacobs, B. L. et al., "Activity of Brain Serotonergic Neurons in the Behaving Animal," Pharmacol. Rev., The American Society for Pharmacology and Experimental Therapeutics, vol. 43, No. 4, 1991, pp. 563-578.

Steriade, M. et al., "Thalamocortical Oscillations in the Sleeping and Aroused Brain," Science, American Association for the Advancement of Science, vol. 262, No. 5134, Oct. 29, 1993, pp. 630, 631 and 679-685.

Webster, H. et al., "Neurotoxic Lesions of the Dorsolateral Pontomesencephalic Tegmentum-Cholinergic Cell Area in the Cat: Effects Upon Sleep-Waking States," Brain Research, Elsevier Science Publishers B.V. Amsterdam, vol. 458, No. 2, 1988, pp. 285-302.

Steriade, M. et al., "Neuronal Activities in Brain-Stem Cholinergic Nuclei Related to Tonic Activation Processes in Thalamocortical Systems," The J. of Neurosci., vol. 10, No. 8, Aug. 1990, pp. 2541-2559.

Khateb, A. et al, "Pharmacological and Immunohistochemical Evidence for a Serotonergic Modulation of Cholinergic Nucleus Basalis Neurons," Eur. J. of Neurosci., vol. 5, 1993, pp. 541-547.

Kleitman, N. "Sleep and Wakefulness," The University of Chicago Press, 1963, 3 pages of Table of Contents.

Moruzzi, G. "The Sleep-Waking Cycle," Reviews of Physiology Biochemistry and Experimental Pharmacology, 1972, pp. 1-65.

Jouvet, M. "The Role of Monoamines and Acetylcholine-Containing Neurons in the Regulation of the Sleep-Waking Cycle," Ergebn, Physical vol. 64, 1972, pp. 166-307.

Sakai, K et al., "The Posterior Hypothalamus in the Regulation of Wakefulness and Paradoxical Sleep," In Mancia, M. et al., "The Diencephalon and Sleep " Raven Press, Ltd., 1990, pp. 171-198.

Sakai, K. "Central Mechanisms of Paradoxical Sleep," C. Midbrain, Brainstem Structures and Stage Setting, vol. 8, 1986, pp. 402-407.

Steriade, M. et al., "Brainstem Control of Wakefulness and Sleep," Plenum Press, 1990, 9 pages of Table of Contents.

Schaltenbrand, G. et al., "Atlas for Stereotaxy of the Human Brain," Academic Press, 6 pages of Table of Contents, 1977.

Schaltenbrand, G., et al., "Introduction to Stereotaxis with an Atlas of the Human Brain," vols. I and II, 1959, 19 pages of Table of Context.

\* cited by examiner

NEUROSTIMULATION FOR AFFECTING SLEEP DISORDERS

CROSS-REFERENCE TO RELATED APPLICATION

This application claims the benefit under 35 U.S.C. §119 (e) of U.S. provisional application Ser. No. 60/353,697 filed Feb. 1, 2002, the entire contents of which are hereby incorporated by reference in their entirety herein.

BACKGROUND OF THE INVENTION

The use of neurostimulation, including deep brain stimulation, and modulation of neural structures for both the excitation and inhibition of the neural elements, provides an effective alternative to today's surgical lesioning techniques in the treatment of sleep disorders. Today's surgical lesioning techniques, while technologically improved and more precise, have the fundamental limitation of being inherently irreversible and are essentially a "one shot" procedure with little chance of alleviating or preventing potential side effects. In addition, there is a limited possibility to provide continuous benefits as the disorder progresses and the patient's symptoms evolve.

It has been recognized that electrical stimulation holds significant advantages over lesioning in the treatment of various disorders, inasmuch as lesioning can only destroy nervous system tissue. In many instances, the preferred effect is to stimulate to increase, decrease, or block neuronal activity. Electrical stimulation permits such modulation of the target neural structures and, equally importantly, does not require the destruction of nervous tissue. In many ways, this is analogous to a reversible and adjustable lesioning procedure.

Sleep is an active process during which many body functions fluctuate, including respiration, temperature, body tone and hormone secretion. A specialized type of sleep, Rapid Eye Movement (REM sleep) is associated with dreaming, fleeting eye movements, muscle twitching, a generalized decrease in body tone, and irregular respiration, heart beat and blood pressure.

It is believed that up to 20% of the general population have sleep disorders. Sleep disorders can include narcolepsy and its clinical manifestations such as sleep attacks, cataplexy, sleep paralysis, hypnagogic hallucinations; insomnia; sleep apnea; hypersomnia; and related disorders. Narcolepsy is a particularly dangerous problem given its incidence of 0.05% in the U.S. population, according to the American Association of Sleeping Disorders.

The Circadian Cycle

Inventions of the light bulb and airplane have greatly enhanced human capability. However, they have also imposed new challenges to human health. Travel across time zones and shift-working schedules are familiar examples of such challenges. Jet lag is often associated with fatigue, daytime sleepiness, loss of appetite, difficulty concentrating, and inability to sleep at night. These symptoms are experienced because the human body is genetically programmed to perform certain physiological functions only at certain times of the day. The variation of physiology around the 24-hour cycle is referred to as circadian rhythm, which is an important behavioral adaptation to the earth's daily rotation.

Circadian rhythms are not merely passive reflections of the environmental light-dark cycle, but instead depend upon an underlying endogenous clock. The suprachiasmatic nucleus (SCN) of the hypothalamus is the mammalian circadian clock that synchronizes the functions of different organ systems to each other and to the environmental light-dark cycle. In addition to the SCN, other structures also influence the human circadian rhythm. The retina is the dominant circadian clock in invertebrates, such as sea slugs. The pineal gland is the dominant circadian clock in birds. In mammals, these ancient circadian pacemakers work in concert with the SCN. Melatonin is a hormone synthesized in the pineal gland and released at night.

Serotonin is an important neurotransmitter involved in the mechanisms related to the generation of the different stages of awakeness-sleep cycle. (Khateb, A. et al., Pharmacological and morphological evidence for a serotoninergic input to cholinergic nucleus basalis neurons. Eur. J. Neurosci, v5, p 541-47, 1993). Previous research has proven that lesions in the Raphe Nucleus, which is rich in serotonin, can produce intense insomnia which is reversed with the injection of serotonin precursors (5-hidroxitriptofano) (Jouvet, M., The role of monoamine and acetylcholine-containing neurons in the regulation of the sleep-waking cycle. Ergebn. Physiol V 64, 165-307, 1972).

It is also known that the serotoninergic fiber (Khateb et al. 1993), which originates from the Raphe Nucleus, together with the noradrenergic fibers, is tonic activated during the alert phase, decreasing its activity during non-REM sleep and remaining silent in REM sleep (Jacobs, B. L.; Fornal. C. A., Activity of brain serotoninergic neurons in the behaving animal. Pharmacol. Ver. 43, 563-78, 1991). Khateb et al. (1993) proved that serotoninergic neurons hyperpolarize colinergic neurons in the Basal Forebrain and noradrenergic neurons promote depolarization of the same neurons located in the Basal Forebrain.

Jouvet et al. in 1984 described a region just ventral to the Locus Coeruleus which lesion causes total inhibition of the motor behavior during the dreams. (Jouvet, M. et al., Etude de la privation selective de la phase paradoxale de sommeil chez le chat. Comptes Rendus de la Societe de Biologie, Paris, 1984.) Later, Sakai named it the Perilocus Coeruleus region or Alfa-Coeruleus nucleus (Sakai, K., Central mechanisms of paradoxical sleep. Brain Development 8, 402-7, 1986.) The lesion of this region cancels the inhibition of the motor neurons during REM sleep and releases the motor manifestation during the dreams (Jouvet et al., 1972).

The Locus Coeruleus and other nuclei located in the posterior portion of the brainstem which are identified infra, have been studied as possible targets. (Gonzalez-Martinez, J A, Doctorate Thesis: Study of the electroscilograms of the olfactory tract of the rat during the awakefull-sleep cycle. University of Sao Paulo Medical School, Sao Paulo, 2002; Jacobs, B. L. and Fornal, C. A., 1991; Jouvet, M., 1972; Jouvet, M, Recherches sur les structures nerveuses et les mecanismes responsables des differentes phases du sommeil physiologic. Arch. Ital. Biol. V100, 125-206, 1962; Jouvet, M.; Vimont, P; Delorme, F. Etude de la privation selective de la phase paradoxale de sommeil chez le chat. Comptes Rendus de la Societe de Biologie, Paris, 1984; Khateb, A. et al., 1993; Kleitman, N., Sleep and Wakefulness. Chicago, The University of Chicago Press, 1963; Moruzzi, G., The sleep-waking cycle. Ergebn Physiol v 64 1-165, 1972; Pompeiano, O., Mechanisms responsible for spinal inhibition during desynchronized sleep: Experimental study. In Guilleminauult, C; Dement, W C; Passouant, P (ed), Advances in Sleep Research, v.3, New York, Spectrum, p 411-49, 1976; Sakai, K., 1986; Sakai, K; El Mansari, M; Lin, J. S; Zhang, G; Vanni-Mecier, The posterior hypothalamus in the regulation of wakefulness and paradoxical sleep. In Mancia, G (ed), The Diencephalon and Sleep, New York, Raven Press, 171-98, 1990; Steriade, M; Datta, S; Pare, D; Oakson, G; Curro Dossi, R., Neuronal activities in the brain stem cholinergic nuclei related to tonic activation processes in thalamocortical systems, J Neurosci, 20, 2541-59, 1990; Steriade, M. and McCarley, R W, Brainstem control of wakefulness and sleep. New York and London, Plenum Press, 1990; Steriade, M. et al., Thalamocortical oscilations in the sleeping and aroused brain. Science, 226, 679-85, 1993; and Webster, H. and Jones, B E, Neurotoxic lesions of the dorsolateral pontomesencephalic tegmentum-cholinergic cell area in the cat. Effects upon sleep-waking states. Brain Res, 458, 285-302, 1988.)

Narcolepsy

Narcolepsy is a disabling illness affecting more than 1 in 2,000 Americans. Most individuals with the disorder are not diagnosed, and are thus, not treated. The disease is principally characterized by a permanent and overwhelming feeling of sleepiness and fatigue. Other symptoms involve abnormalities of dreaming sleep, such as dream-like hallucinations and finding oneself physically weak or paralyzed for a few seconds.

Studies have shown that even treated narcoleptic patients are often markedly psychosocially impaired in the area of work, leisure, interpersonal relations, and are more prone to accidents. These effects are even more severe than the well-documented deleterious effects of epilepsy when similar criteria are used for comparison.

The large majority of narcoleptic patients in this country are still undiagnosed, and narcoleptic subjects are most often diagnosed only after many years of struggle. In one recent study, the mean number of years between the onset of symptoms and correct diagnosis was 14 years. Since the symptoms of narcolepsy usually appear during adolescence, this means that most narcoleptic patients are diagnosed too late to prevent the dramatic impact of the disease on their personal and professional development.

The main symptoms of narcolepsy are excessive daytime sleepiness and abnormal REM sleep, i.e., intrusion of REM sleep into the waking state or into the transition periods between waking and sleep. Many narcoleptics are sleepy during most or all of the day, specifically during times when normal people may only have a tendency to become somnolent. An example would be the tendency of a normal person to become somnolent after a heavy meal, whereas a narcoleptic would fall asleep.

Patients with narcolepsy are subject to narcoleptic sleep attacks, cataplexy, sleep paralysis and hypnagogic hallucinations; however, an individual patient may not have all these symptoms. Sleep attacks may occur at any time the day and in embarrassing and dangerous situation, such as while walking, climbing a ladder or even driving. These attacks are brief but can occur anytime and in any situation. Narcolepsy is not only a serious and common medical problem, it also offers basic sleep researchers a unique opportunity to gather new information on the central mechanisms regulating REM sleep and alertness. Since the 1960s it has been known that several of the disabling symptoms of narcolepsy, such as sleep paralysis, cataplexy and hypnagogic hallucinations, are pathological equivalents of REM sleep.

Sleep paralysis, it is the loss of tone, such as that which occurs during an episode of REM sleep, but it occurs when the patient is awake. Its consequences are relevant and extremely dangerous. A frightening symptom considered to be an abnormal episode of REM sleep atonia, the patient suddenly finds himself unable to move for a few minutes, most often upon falling asleep or waking up. During hypnagogic hallucinations, patients experience dream-like auditory or visual hallucinations, while dozing or falling asleep. Cataplexy, a pathological equivalent of REM sleep atonia unique to narcolepsy, is a striking, sudden episode of muscle weakness triggered by emotions. Cataplexy is characterized by loss of body tone without loss of consciousness. Typically, the patient's knees buckle and may give way upon laughing, elation, surprise or anger. In other typical cataplectic attacks the head may drop or the jaw may become slack. In severe cases, the patient might fall down and become completely paralyzed for a few seconds to several minutes. Reflexes are abolished during the attack.

Narcolepsy can be diagnosed using specific medical procedures. The diagnosis of narcolepsy is usually easy if all the symptoms of the illness are present. More often, however, the symptoms of dissociated REM sleep such as cataplexy are mild. In such cases, a nocturnal polysomnogram, followed by the multiple sleep latency test (MSLT), is suggested. This test, performed at a sleep disorders clinic, will confirm the daytime sleepiness by showing a short sleep latency of usually less than 5 minutes, as well as an abnormally short latency prior to the first REM period (SOREMPs). Other causes of daytime sleepiness, such as sleep apnea or periodic leg movements, are also excluded by the nocturnal recordings.

In the current treatment of narcolepsy, no single therapy will control all the symptoms. The narcolepsy responds best to strategically placed 15 to 20 minutes naps and the use of stimulants drugs (e.g., dextraamphetamine sulfate or methylphenidate hydrochloride (Ritalin), or pemoline) and a tricyclic antidepressant (e.g., imipramine or clormipramine). The combined use of these stimulants and tricyclic antidepressant drugs is often indicated. The occurrence of tolerance is frequent and the treatment fails quite often. Moreover, the stimulants drugs and the tricyclic antidepressants increase the level of cathecolamines, and their chronic administration may produce hypertension.

Sleep Apnea

Sleep Apnea is a disorder of breathing during sleep. Typically it is accompanied by loud snoring. Apnea during sleep consist of brief periods throughout the night in which breathing stops. People with sleep apnea do not get enough oxygen during sleep. There are two major types of apnea: obstructive sleep apnea and central sleep apnea.

Obstructive sleep apnea is the most common type and is due to an obstruction in the throat during sleep. Bed partners notice pauses of approximately 10 to 60 seconds between loud snores. The narrowing of the upper airway can be a result of several factors including inherent physical characteristics, excess weight, and alcohol consumption before sleep.

Central sleep apnea is caused by a delay in the signal from the brain to breath. With both obstructive and central apnea, the subject suffering therefrom must wake up briefly to breathe, sometimes hundreds of times during the night. Usually there is no memory of these brief awakenings. This type of sleep apnea can be treated with electrical stimulation of the above-mentioned nuclei.

The treatment of sleep apnea is governed by the severity of symptoms and the type of apnea (central or obstructive). In central apnea, trazadone has been reported to have some effects on the treatment of the symptoms. Other medications may include acetazolamide, theophylline and clomipramine, which have produced questionable results.

Insomnia

Insomnia is a sleep disorder that comes in many different manifestations and symptoms, including difficulty falling asleep, no problem falling asleep but difficulty staying asleep, i.e., many nocturnal awakenings, or even waking up too early. Normally a normal adult without any stress factors needs from 7 to 9 hours of good quality of sleep; the actual amount of sleep needed varies from person to person.

There are three basic types of insomnia: 1) transient insomnia, which last for a few nights; 2) short-term insomnia, in which poor sleep lasts from two to four weeks of poor sleep; and 3) chronic insomnia, in which poor sleep occurs most nights and may last a month or longer.

Transient and short-term insomnia generally occur in people who are temporarily experiencing one or more of the following: stress, environmental noise, extreme temperatures, change in the surrounding environment, sleep/wake schedule problems such as those due to jet lag or medication side effects, for example.

Chronic insomnia is more complex and often results from a combination of factors, including underlying physical or mental disorders. One of the most common causes of chronic insomnia is depression. Other underlying causes include arthritis, kidney disease, heart failure, asthma, sleep apnea, restless legs syndrome, Parkinson's disease, and hyperthyroidism. However, chronic insomnia may also be due to behavioral factors, including the misuse of caffeine, alcohol, or other substances; disrupted sleep/wake cycles as may occur with shift work or other nighttime activity schedules; and chronic stress.

Treatment of Transient and Short-Term Insomnia

Transient and short-term insomnia may not require treatment since episodes last only a few days at a time. For example, if insomnia is due to a temporary change in the sleep/wake schedule, as with jet lag, the person's biological clock will often get back to normal on its own. However, for some people who experience daytime sleepiness and impaired performance as a result of transient insomnia, the use of short-acting sleeping pills may improve sleep and next-day alertness. As with all drugs, there are potential side effects. The use of over-the-counter sleep medicines is not usually recommended for the treatment of insomnia.

Treatment of Chronic Insomnia

Treatment for chronic insomnia first consists of diagnosing and treating underlying medical or psychological problems. Further treatment includes identifying a patient's behavior(s) that may worsen insomnia and advising the patient to stop or reduce such behavior. Finally, sleeping pills may be prescribed, however, the long-term use of sleeping pills for chronic insomnia is controversial.

Jet Lag Syndrome

Jet lag, also called desynchronosis, is a temporary condition that some people experience following air travel across several time zones in a short period of time. Jet lag causes the traveler's internal clock to be out of sync with the external environment. People experiencing jet lag have a difficult time maintaining their internal, routine sleep-wake pattern in their new location, because external stimuli, such as sunshine and local timetables, dictate a different pattern. For this reason, the person experiencing jet lag can feel lethargic one moment and excited the next. Jet lag creates a double bind for vacationers and business people who must cross several time zones to reach their destination, but who are also intent on maximizing sightseeing or productivity. As travelers attempt to adjust their internal clock to a new external environment, symptoms result with varying intensity.

Jet lag occurs while rapidly crossing time zones, or, more specifically, it occurs after crossing the Earth's meridians. Meridians demarcate geographic position in relation to the Earth's poles and, ultimately, define time zones. Jet lag is a unique sleep disorder because its onset is not necessarily caused by abnormal sleep patterns, like insomnia. Therefore, travelers who sleep normally prior to transmeridian travel are not immune to jet lag. Again, the symptoms of jetlag result when a person's internal clock attempts to acclimate to a new external environment. This acclimation involves circadian rhythms that, among other functions, are associated with the body's management of sleep.

In addition to the "tired-wired," "soar-crash" feeling that travelers experience after long, rapid air travel, there are numerous symptoms that may occur with jet lag, such as insomnia, daytime fatigue, stomachaches, headaches, irritability, and decreased awareness. The degree of disruption varies greatly among people; some may not be bothered at all. Jet lag is a transient sleep disorder and is classified differently than other, more serious disorders. Although jet lag occasionally lasts for a week or more, travelers usually return to their normal sleep-wake pattern after a day or two. For many travelers, jet lag can catalyze the effects of certain conditions associated with the head and nervous system that are not related to specific sleep-wake patterns. For example, many symptoms attributed to jet lag are actually caused by the environment of the airplane, e.g., dry air due to very low humidity in an airplane, pressurization, noise, vibrations, and a cramped environment. These symptoms may include dry eyes, dry and irritated nose and sinuses, headaches, earaches, muscle cramps, and abdominal distention (bloating). Occasionally, dizziness or swollen feet and ankles may occur.

The treatment of Jet Lag syndrome is still a matter of debate since no clear therapeutic effect has been observed with any drug or behavioral treatment. Melatonin is the hormone produced in the pituitary gland that may act "re setting" the biological clock of the hypothalamus and controlling the symptoms. Unfortunately, there is a lack of scientific data in respect of the use of this hormone in the treatment of Jet Lag or any other disease.

The causes of the above-described sleep disorders include the sudden intrusion of the REM sleep during the awake period. Hence, the rationale of the presently provided methods of treatment is to abort or activate REM sleep by modulating specific nuclei in the brain stem, depending upon the sleep disorder or abnormal awakeness-sleep cycle to be treated, as discussed infra. Several papers highlight the role of Locus Coeruleus in the generation of REM Sleep. The inhibition of this specific nucleus in experimental trials interrupts the REM Sleep and its clinical manifestations, thus controlling and avoiding the dangerous consequences of those sleep disorders. The same neurophysiological response happens when lesions are provoked in this nucleus or related nuclei.

The Locus coeruleus, a small noradrenergic nucleus, and the Nucleus Reticularis Pontis Oralis and Caudalis (NRPO and NRPOC) have been described as the main relay for the generation of REM sleep. (Jouvet, M. The role of monoamine and acetylcholine-containing neurons in the regulation of the sleep-waking cycle. Ergebn. Physiol V 64, 165-307, 1972).

SUMMARY OF THE INVENTION

In one aspect this invention provides a method of affecting a sleep disorder in a subject having the sleep disorder, said method comprising: a) identifying at least one nucleus in a brain of the subject, said nucleus being a nucleus of the sleep circuitry of the brain; and b) stimulating the at least one identified nucleus so as to modulate the nucleus, thereby affecting the sleep disorder.

In another aspect, the present invention provides a method of re-establishing a normal awakeness-sleep cycle in a subject having an abnormal awakeness-sleep cycle, said method comprising: a) identifying at least one nucleus in a brain of the subject, said nucleus being a nucleus of the sleep circuitry of the brain; and b) stimulating the at least one identified nucleus so as to modulate the nucleus, thereby re-establishing the normal awakeness-sleep cycle in the subject.

In a further aspect, the present invention provides a use of an electrode system adapted to be implanted within a brain of a subject having a sleep disorder, wherein the electrode is implanted proximate to at least one nucleus of the brain, said nucleus being a nucleus of the sleep circuitry of the brain, and provided with a stimulation signal to stimulate the at least one nucleus to affect the sleep disorder.

In another aspect, the present invention provides a use of an electrode system adapted to be implanted within a brain of a subject having a sleep disorder for affecting the sleep disorder.

In a further aspect, the present invention provides a use of a chemical stimulus to be infused into a brain of a subject having a sleep disorder, wherein the chemical stimulus is infused proximate to at least one nucleus of the brain, said nucleus being a nucleus of the sleep circuitry of the brain, to affect the sleep disorder. The chemical stimulus may be a neurotransmitter, a neurotransmitter mimic, an agent for affecting sleep disorders or abnormal awakeness-sleep cycles, including but not limited to those listed drugs in Table 2 infra.

In another aspect, the present invention provides a use of an electrode system adapted to be implanted within a brain of a subject having an abnormal awakeness-sleep cycle, wherein the electrode is implanted proximate to at least one nucleus of the brain, said nucleus being a nucleus of the sleep circuitry of the brain, and provided with a stimulation signal to stimulate the at least one nucleus to affect the abnormal awakeness-sleep cycle. As used herein, proximate is defined to mean at or near the vicinity of the identified nucleus.

In another aspect, the present invention provides a use of an electrode system adapted to be implanted within a brain of a subject having an abnormal awakeness-sleep cycle for affecting the abnormal awakeness-sleep cycle.

In another aspect, the present invention provides a use of a chemical stimulus to be infused into a brain of a subject having an abnormal awakeness-sleep cycle, wherein the chemical stimulus is infused proximate to at least one nucleus of the brain, said nucleus being a nucleus of the sleep circuitry of the brain, to affect the abnormal awakeness-sleep cycle.

Still further aspects of the present invention will become apparent to those of ordinary skill in the art upon reading and understanding the following detailed description of the preferred embodiments.

DESCRIPTION OF THE DRAWINGS

The invention may take form in various components and arrangements of components and in various steps and arrangements of steps. The drawings are only for purposes of illustrating the preferred embodiments and are not to be construed as limiting the invention.

DETAILED DESCRIPTION OF THE PREFERRED EMBODIMENTS

Figure 1:
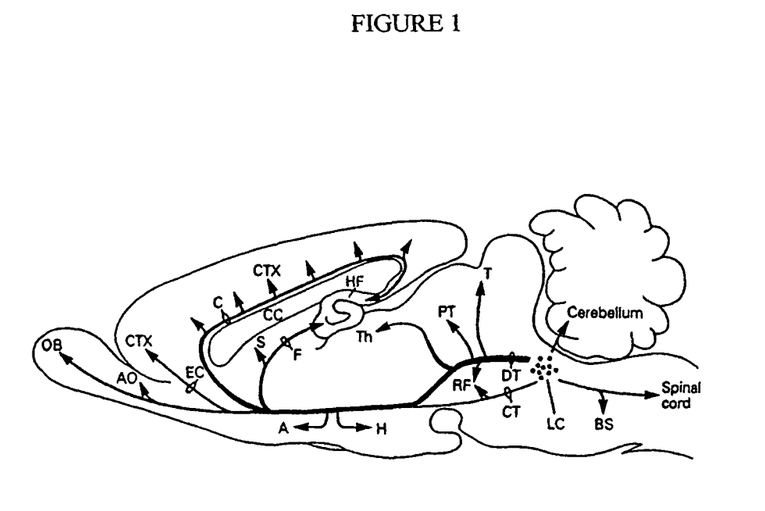
FIG. 1 illustrates the noradrenergic connections of the Locus Coeruleus in the several central nervous system relay involved in the regulation of the awakefulness-sleep cycle. LC: locus coeruleus. RF: Dorsal raphe nucleus. T: Thalamus. H: Posterior hypothalamus. CTX: Cortex.
Figure 2:
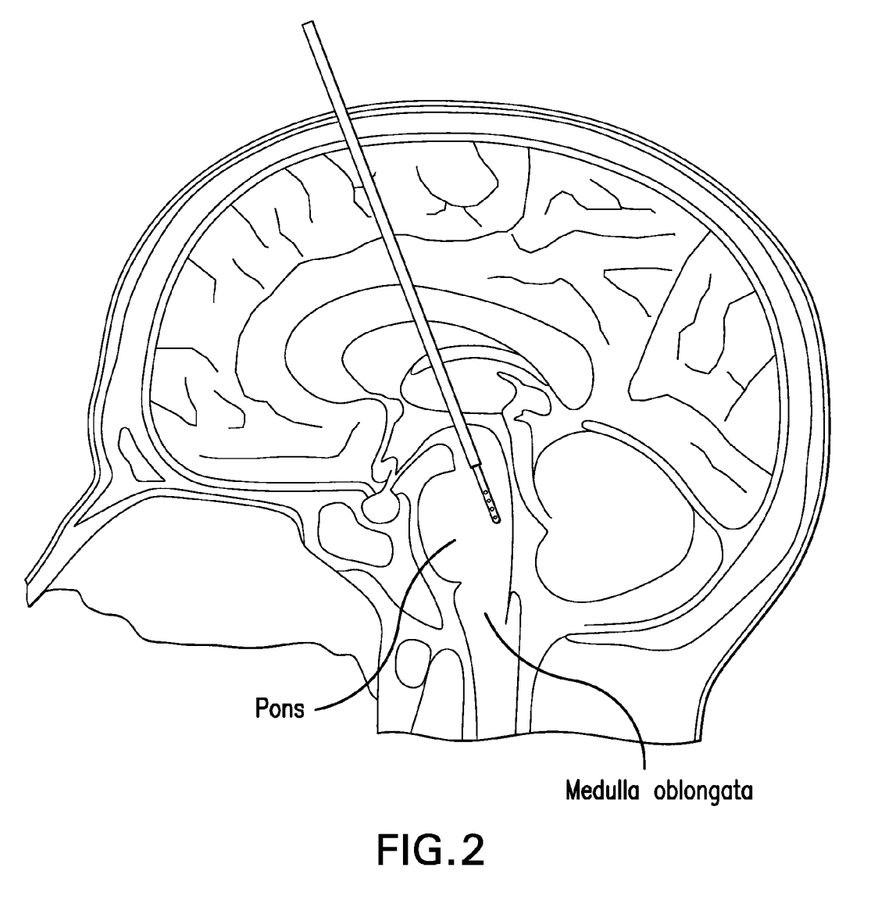
FIG. 2 shows the medial surface of the brain. Also illustrated is a deep brain electrode inserted into the Locus Coeruleus Nuclei. A cannula which has a directional ball at the tip to allow angulation of the electrode may be used as shown.

Surgical treatments for the above-described sleep disorders that have traditionally been treated by behavioral therapy or drugs, have been largely limited to stereotactic lesioning, such as cingulotomy, capsulotomy, subcaudate tractotomy, and limbic leucotomy. Such procedures have also been applied to date in the treatment of affective disorders and anxiety disorders. If one critically examines the results of these procedures in the literature, it becomes apparent, when applied to a carefully selected patient population in conjunction with modern stereotactic surgical equipment and imaging techniques, that these procedures are both efficacious and safe. In fact, in a certain subset of patients who have failed all conventional treatments, these neurosurgical procedures may be the only treatment options available. Therefore, electrical and/or chemical neurosurgical neuromodulating techniques, with their inherent reversibility and adjustability, offer a safer and potentially more effective alternative to lesioning procedures.

The present invention finds particular utility in its application to sleep disorders manifesting in humans. However, it is also to be appreciated that the present invention is applicable to other animals which exhibit behavior that is modulated by the brain. This may include, for example, primates, canines, felines, elephants, dolphins, etc. Utilizing the various embodiments of the present invention, one skilled in the art may modulate the functional outcome of the brain to achieve a desirable result. As used herein modulation/modulating includes changing an existing pattern of brain (e.g., including identified nuclei of the sleep circuitry of the brain) activity by electrical and/or chemical stimulation, wherein said pattern is an abnormal pattern, i.e., not found in subject who does not suffer from a sleep disorder or an abnormal awakeness-sleep cycle, as well as activating or inhibiting a specific nucleus.

One technique that offers the ability to affect neuronal function in a reversible and dynamic fashion is the delivery of electrical stimulation for neuromodulation directly to target tissues via an implanted electrode assembly.

Another technique, which offers the ability to affect neuronal function in a reversible and dynamic fashion, is the delivery of drugs or neuromodulating chemicals directly to target tissues via a subcutaneously implanted pump and/or a slow release matrix. Such drugs, listed in Table 2 infra, including either traditional disorder-treating agents, neurotransmitters or chemicals mimicking neurotransmitters, or combinations thereof, may be precisely administered by the methods described herein to the target nuclei at such low doses as to completely avoid the side effects so common to modern pharmacotherapy and to provide a physiological neuromodulation. Such doses may also be tailored in magnitude with respect to a particular patient's varying symptomatology. A chemical neuromodulating system may also be implanted as a primary treatment strategy or in combination with an electrically based one.

A combination therapeutic approach provided herein, one combining electrical and chemical means, would be penultimate to generating healthy neuronal tissue itself. In addition to the stimulation and chemical modulation, an implantable device may be configured to also have chemical and/or electrical sensing functions that are coupled to the chemical and electrical output of the modulating device.

Initially there is an impetus to treat sleep disorders with direct modulation of activity in that portion of the brain causing the disorder. In this regard there have been a number of studies that have helped to identify the neural structures and their precise connections which are implicated in causing these disorders. These are the structures that are functioning abnormally and manifesting in the particular disorder. Numerous anatomical studies from autopsies, animal studies, and imaging such as computerized tomography (CT) scans, and magnetic resonance imaging (MRI) scans have demonstrated the role of these structures and their connections in psychiatric activity/disorders. In addition to these anatomical studies, a number of physiological techniques and diagnostic tools are used to determine the physiological aberrations underlying these disorders. This includes electrical methods such as electroencephalography (EEG), magnetoencephalography (MEG), as well as metabolic and blood flow studies such as functional magnetic resonance imaging (fMRI), and positron emission tomography (PET). The combination of the anatomical and physiological studies have provided increased insight into our understanding of the structures which are involved in the normal functioning or activity of the brain and the abnormal functioning manifesting in these disorders.

Methods and systems using fusion of functional and structural medical imaging for localizing targets in the body and guiding diagnostic or therapeutic instruments toward a target region in the body have been described in U.S. Pat. No. 6,368,331, issued on Apr. 9, 2002 to Front et al., U.S. patent application Publication No. US 2002/0032375, published Mar. 14, 2002 by Bauch et al., and U.S. patent application Publication No. US 2002/0183607, published Dec. 5, 2002 by Bauch et al., all of which are hereby incorporated by reference in their entireties. Methods for target localization specifically within the nervous system, including the brain, have been described in U.S. Provisional Application No. 60/353,695, filed Feb. 1, 2002, by Rezai et al. which is hereby incorporated by reference in its entirety. Specifically, provided in U.S. Provisional Application No. 60/353,695 is a method of medical imaging, comprising: placing a fiducial marker proximate to an area of a body to be imaged; obtaining a first image of the area of the body using a first medical imaging technique, the first image including a first image of the fiducial marker; obtaining a second image of the area of the body using a second medical imaging technique, the second image including a second image of the fiducial marker, the second medical imaging technique being different than the first medical imaging technique; superimposing the first image of the area of the body and the second image of the area of the body; and aligning the first image of the first fiducial marker with the second image of the fiducial marker. Useful medical imaging techniques to obtain functional images include but are not limited to functional MRI, PET or MEG. Useful medical imaging techniques to obtain structural images include but are not limited to volumetric MRI, CT. The methods described therein may be applied to target nuclei for modulation by the presently described methods of affecting sleep disorders and abnormal sleep-awakeness cycles.

The present invention provides methods which use a neurostimulation device in order to affect sleep disorders to regulate, prevent, treat, alleviate the symptoms of and/or reduce the effects of such sleep disorders. Also provided are methods which use chemical stimulation in order to affect sleep disorders.

In a preferred embodiment, the methods of affecting a sleep disorder in a subject having the sleep disorder comprise: a) identifying at least one nucleus in a brain of the subject, said nucleus being a nucleus of the sleep circuitry of the brain; and b) stimulating the at least one identified nucleus so as to modulate the nucleus, thereby affecting the sleep disorder.

As used herein a nucleus or nuclei, are defined as a concentration of neurons in the brain or a union of neurons.

More specifically, the following stereotactic targets for affecting sleep disorders are identified and stimulated: the Locus Coeruleus, Dorsal Raphe Nucleus, Posterior Hypothalamus, Supra-Chiasmatic Nucleus of Hypothalamus, Nucleus Reticularis Pontis Oralis and Caudalis, and Basal Forebrain. The above-described nuclei are located in the posterior portion of the brainstem, close to the fourth ventricle (Nucleus Coeruleus) or in the base of the encephalus and can be reached using conventional stereotactic functional neurosurgical methods.

In one embodiment of this invention, stimulation of the above nuclei, including the Locus Coeruleus, can also be performed in order to re-establish a normal awakeness-sleep cycle in pathologies related to a disjunction of the normal circadian cycle (narcolepsy, imnsonia) or even respiratory disturbance during the awakeness-sleepness cycle (sleep apnea). The methods described herein may further be utilized to affect patients with an abnormal awakeness-sleepness cycle, such as severe jet lag phenomenon, sleep deprivation or side effects of medication(s), to regulate, prevent, treat, alleviate the symptoms of and/or reduce the effects of such an abnormal awakeness-sleepness cycle. Similarily, any of the related nuclei in the circuitry of sleep, enumerated supra, may also be modulated to achieve a desired effect to affect any of the above-described disorders.

Modulation of the Locus Coeruleus and related nuclei, described supra, by the methods described herein may include electrical stimulation or inhibition, chemical modulation via an infusion system, or both electrical and chemical stimulation or inhibition. An electrode system which may be used to effect electrical stimulation is described infra.

In another embodiment of this invention, at least one sensor, which may be a cortical or subcortical sensor, e.g., subdural electrodes, may also be used to monitor the brain's sleep rhythms in order to allow for a closed-loop feedback and autoregulation of the system. Further sensory monitors may also include internal or external vital sign monitors for heart rate, respiration, REM, body tone, brain activity, etc. Brain activity may be monitored by electrocorticography. An example of this latter method of treatment using a closed-loop feedback system includes a system for Narcolepsy in which sensor(s) monitor the brain's sleep rhythm and result in inhibition of the Locus Coeruleus if the sensor(s) detect that the brain is approaching REM sleep (a particular sleep pattern phase). This system would be programmed to be in an off mode at night to encourage physiological sleep.

Conversely, a closed-loop feedback system may be used monitor the brain's sleep rhythm, wherein detection of a correct/particular sleep pattern phase results in activation of the identified the nucleus/nuclei at the appropriate time, e.g., in jet lag, detection of a sleep pattern requiring activation/excitation of the nuclei would result in activation of the Locus Coeruleus. Sleep pattern phases are well known to one of skill in the art.

Table 1 summarizes the sleep circuitry nuclei which require either inhibition, activation, or modulation depending upon the particular disease to be affected.

TABLE 1

Possible modulation type of the sleep circuitry nuclei in relation to the respective pathology.
+: Excitation; −: Inhibition or Modulation.

|  | Narcolepsy | Insomnia | Sleep apnea | Jet Lag |
|---|---|---|---|---|
| Locus Coeruleus | − | +/− | +/− | +/− |
| Dorsal Raphe Nucleus | − | + | +/− | +/− |
| Nucleus Reticularis Pons | − | + | +/− | +/− |

TABLE 1-continued

Possible modulation type of the sleep circuitry nuclei in relation to the respective pathology.
+: Excitation; −: Inhibition or Modulation.

|  | Narcolepsy | Insomnia | Sleep apnea | Jet Lag |
|---|---|---|---|---|
| Posterior Hypothalamus | − | + | +/− | +/− |
| Basal Forebrain | − | + | +/− | +/− |
| Suprachiasmatic Nucleus | +/− | +/− | +/− | + |

Coordinates for target sites to be stimulated for treatment of sleep disorders may be obtained from atlases of the brain, including Schaltenbrand, G. and Bailey, P., 1959, Introduction to Steroetaxis, with an Atlas of the Human Brain, G. Thieme, Stuttgart; Schaltenbrand, G. and Wahren, W., 1977, Atlas for Stereotaxy of the Human Brain, Theime, Stuttgart; Mai, J. K., J. Assheuer and G. Paxinos, 1997, Atlas of the Human Brain, Academic Press, the entire contents of which are incorporated by reference herein in particular the coordinates. Stereotactic coordinates for the nuclei involved in sleep circuitry which may be stimulated by the methods are provided below.

Stereotactic Coordinates

The stereotactic coordinates for several nuclei in the sleep circuitry of the brain, relative to the AC-PC Line, are as follows:
Locus Coeruleus
    Axis X (Medial-lateral): 0 to 6 mm from Mid AC-PC line
    Axis Y (Antero-Posterior): 5-9 mm Posterior to PC
    Axis Z (Dorsal-Ventral): 7-17 mm from Mid AC-PC line
Dorsal Raphe Nucleus
    Axis X (Medial-lateral): 0 to 8 mm from Mid AC-PC line
    Axis Y (Antero-Posterior): 3-9 mm Posterior to PC
    Axis Z (Dorsal-Ventral): 2-10 mm from Mid AC-PC line
Nucleus Reticulares Pontis Oralis/Caudalis
    Axis X (Medial-lateral): 0 to 6 mm from Mid AC-PC line
    Axis Y (Antero-Posterior): 2-8 mm Posterior to PC
    Axis Z (Dorsal-Ventral): 5-22 mm from Mid AC-PC line
Posterior Hypothalamus
    Axis X (Medial-lateral): 0 to 6 mm from Mid AC-PC line
    Axis Y (Antero-Posterior): 8-14 mm Posterior to AC
    Axis Z (Dorsal-Ventral): 0-8 mm from Mid AC-PC line
Basal Forebrain
    Axis X (Medial-lateral): 0 to 20 mm from Mid AC-PC line
    Axis Y (Antero-Posterior): 0-36 mm Anterior to AC
    Axis Z (Dorsal-Ventral): 0-25 mm from Mid AC-PC line
Supra-Chiasmatic Nucleus
    Axis X (Medial-lateral): 0 to 10 mm from Mid AC-PC line
    Axis Y (Antero-Posterior): 8-14 mm Anterior to AC
    Axis Z (Dorsal-Ventral): −5 to +25 mm from Mid AC-PC line One embodiment of the present invention relates generally to modulating the pathological electrical and chemical activity of the brain by electrical stimulation and/or direct placement of neuromodulating chemicals within the corresponding areas of abnormal function and activity. In accordance with this embodiment of the present invention, a method is provided for surgical treatment of disorders by implantation of stimulating electrodes and/or drug or chemical delivery by microinfusion at the locations detailed herein. In preferred embodiments, chemicals may be delivered by a pump or slow release matrix. Pumps which may be used in the present methods include commercially available pumps such as the Synchromed pump manufactured by Medtronic, Inc., as well as any commercially available micropumps. The slow release matrix, also commercially available may be implanted subcutaneously in the skull of the subject, wherein the chemical is infused proximate to the identified nucleus.

In one embodiment of the invention wherein stimulating is effected by electrical and chemical stimulation, the proximal end of the electrode and/or catheter is coupled to an electrical signal source and/or drug delivery pump which, in turn, is operated to stimulate the predetermined treatment site in regions described above such that the desired functional outcome is achieved or the clinical effects of the sleep disorders are reduced.

Sleep disorders which may be affected by the methods described herein include but are not limited to narcolepsy, whose symptoms are manifested by at least one of sleep attacks, sleep paralysis, cataplexy, or hypnagogic hallucinations; insomnia; sleep apnea; hypersomnia; and jet lag phenomenon. Abnormal awakeness-sleep cycles which may also be affected by the methods provided herein, include but are not limited to sleep deprivation, jet lag and side effects of medication(s).

The methods of the present invention in which stimulation is effected by electrical stimulation may be performed by an electrode system. The electrode system includes a cannula which can redirect the electrode in a direction to allow maximal coverage of the Locus coeruleus. The impulse generator of the electrode system must include an internal synchronizable clock which can be externally programmed via telemetry in order to resynchronize sleep patterns. Synchronizable clocks, i.e., timed systems which are programmed to turn on and off at a particular time(s) to be in sync with the body's physiology are known and available for stimulation systems, e.g., such as those used for treatment of epilepsy.

Currently available neuromodulation electrodes, e.g., such as those manufactured by Medtronic, Inc. and described in U.S. Pat. No. 6,356,784, issued Mar. 12, 2002 to Lozano et al, which is hereby incorporated by reference in its entirety, may be used in the methods of the present invention. Commercially available DBS electrode leads manufactures by Medtronic, Inc. may be employed in the methods described herein. Alternatively, electrodes may be custom designed, to be cylindrical, ovoid, plate or grid like electrodes. The stimulation parameters include monopolar, bipolar or multipolar, intensities of 0.1 µV to about 20 V intensity, frequency off 2 Hz to about 2500 Hz, pulse width of 10 microseconds to about 1,000 microseconds. This range of electrical intensities may be used to effectively stimulate the various identified nuclei of the brain to affect sleep disorders using the methods provided herein.

With respect to particular details of electrical stimulation according to the present invention, once the stimulator (i.e. electrode) is secured in place within the brain proximate to the identified nucleus of the brain, the stimulation controller (i.e. pulse generator) is activated thereby applying to the target site an oscillating electrical signal having specified pulsing parameters. The oscillating electrical signal may be applied continuously or intermittently and the pulsing parameters, such as the pulse width, amplitude, frequency, voltage, current, intensity, pole combinations, and/or waveform may be adjusted to affect a desired result. Preferably, the oscillating electrical signal is operated at a voltage between about 0.1 µV to about 20 V. More preferably, the oscillating electrical signal is operated at a voltage between about 1 V to about 15 V. Preferably, the electric signal is operated at a frequency range between about 2 Hz to about 2500 Hz. More preferably, the electric signal is operated at a frequency range between about 2 Hz to about 200 Hz. Preferably, the pulse width of the oscillating electrical signal is between about 10 microseconds to about 1,000 microseconds. More preferably, the pulse width of the oscillating electrical signal is between about 50 microseconds to about 500 microseconds. The waveform may be, for example, biphasic square wave, sine wave, or other electrically safe and feasible combination. Preferably, the application of the oscillating electrical signal is: monopolar when the electrode is monopolar, bipolar when the electrode is bipolar, and multipolar when the electrode is multipolar.

For example, a grid electrode, such as subdural grids manufactured by AD-Tech in different sizes and shapes, which can remain supracortically, and optionally have one or more intracranial extensions, may be used to deliver electrical stimulation to the target nuclei in the methods of the present invention.

Chemicals such as neurotransmitters, including but not limited to acetylcholine, dopamine, epinephrine, norepinephrine, serotonin, GABA, and inhibitors of noradrenaline, or any agent for affecting a sleep disorder or mixtures thereof may be delivered to the identified target nuclei by commercially available catheters and cannulas, e.g., such as those presently used for vascular surgery for aneurysms, which may be modified for drug delivery. Additional catheters which may be used in the present methods include a catheter described in U.S. Pat. No. 6,356,784 to Lozano et al., which is incorporated by reference in its entirety herein. Any commercially available microcannulas/microcatheters, such as those used in microdialysis procedures, may be used to deliver drugs in the methods of the present invention. Table 2 provides a list of neurotransmitters and drugs known to act on the central nervous system, in the circuitry of the awakeness-sleep cycle, which may be delivered to the identified nuclei to affect sleep disorders using the methods of the present invention. The neurotransmitters delivered will vary according to the type of sleep disorder to be affected and the nuclei proximate to which the chemicals are infused.

Table 2. List of possible neurotransmitters and drugs with action in the central nervous system, in the circuitry involved in the regulation of the awakeness-sleep cycle. (Goodman and Gilman's—The Pharmacological Basis of Therapeutics. Pergamon Press, New York, 1990 which is incorporated by reference in its entirety herein, in particular the neurotransmitters and drugs and their effects in the central nervous system.)

Cholinergic agonists: Dimethylphenylpierazinium, Oxotremorine, Muscarine, McN-A-343, Bethanecol, Nicotine.

Cholinergic antagonists: Trimethaphan, atropine, pirenzepine, atropine, hexahydrosiladifenidol, Quinuclidynil, benzoate, pirezepine, Dihydro-B-erythroidine.

Inhibitor of the colinesterase enzyme.

Adrenergic antagonists: Alpha adrenergic antagonists: Phenoxybenzamine; Beta adrenergic antagonists: Propranolol, Metoprolol, praxosin, Rawolscine, yohimbine, metoprolol, practolol, butoxamine, phenyllephrine, clonidine, dobutamine, terbutalina.

Adrenergic agonists: Reserpine, imipramine, methyldopa, amphetamine, cocaine.

Serotoninergic agonists: 5-hydroxitriptamin, LSD, 8-OH DPAT, 5-HT2, 5-HT3.

Serotoninergic antagonists: Metergoline, Spiperone methysergide, MDL-7222

Dopaminergic agonists: L-dopa, SKF 38393, apomorphine; quimpirole

Dopaminergic antagonists: neuroleptics, SCH 23390, Butyrophenones, S-sulpiride

Gabaergic agonists: Muscinol, Bacoflen

Gabergic antagonists: Biccuculine, picrotoxin

Glutamate agonists: Quisqualate, AMPA, NMDAspartate, Kainate

Glutamate antagonists: CNQX, CPP, Lactonized kainite

For combination treatment effected by electrical and chemical stimulation, any of the above-described chemicals may be microinfused using a device comprising an electrode device and a microcatheter. The electrode-microcatheter system used in the methods described herein may be configured to have multiple ports for drug delivery, and may include a recording/multi-contact stimulating electrode, as described by in U.S. Pat. No. 5,676,655, issued on Oct. 14, 1997 to Howard, III et al., which is incorporated by reference in its entirety herein.

Effective doses of the administered chemicals will vary from patient to patient depending upon the sleep disorder to be affected, however, the range of effective doses includes from 0.1 nL to 1 cc in each bolus or in continuous injection.

In still another embodiment, the electrode device which may be used in the above-described methods may further comprise at least one of a pH probe, a sensor to detect bleeding, and oximetry systems to optimally alter the delivery of the modulator (electric or chemical stimulation) in a closed-loop manner.

Although the invention has been described with reference to the preferred embodiments, it will be apparent to one skilled in the art that variations and modifications are contemplated within the spirit and scope of the invention. The drawings and description of the preferred embodiments are made by way of example rather than to limit the scope of the invention, and it is intended to cover within the spirit and scope of the invention all such changes and modifications.

What is claimed is:

1. A method of affecting a sleep disorder in a subject having the sleep disorder said method comprising:
   a) identifying at least one nucleus in a brain of the subject, said nucleus being a nucleus of the sleep circuitry of the brain;
   b) directly stimulating the at least one identified nucleus so as to modulate the nucleus, thereby affecting the sleep disorder, the at least one identified nucleus selected from the group consisting of the locus coeruleus, the dorsal raphe nucleus, the posterior hypothalamus, the suprachiasmatic nucleus of the hypothalamus, the nucleus reticularis pontis oralis, the nucleus reticularis pontis caudalis, and the basal forebrain; and
   c) providing an impulse generator including an internally synchronizable clock for re-synchronizing the patient's sleep patterns, wherein the clock activates stimulation of the at least one identified nucleus to synchronize the patient's abnormal sleep patterns with a normal sleep pattern.

2. The method of claim 1, wherein the stimulating is effected by electrical stimulation.

3. The method of claim 2, wherein the electrical stimulation is performed by an electrode system.

4. The method of claim 3, further comprising: synchronizing the electrode system with the internally synchronizable clock to activate the system at at least one time point.

5. The method of claim 4, wherein the electrode is implanted within the brain proximate to the at least one identified nucleus.

6. The method of claim 1, wherein the stimulating is effected by chemical stimulation.

7. The method of claim 6, wherein the chemical stimulation is performed by a pump or slow release matrix.

8. The method of claim 7, wherein the pump or slow release matrix is subcutaneously implanted in the skull of the subject, and wherein the chemical is infused proximate to the at least one identified nucleus.

9. The method of claim 8, wherein the chemical is a neurotransmitter, a neurotransmitter mimic, an agent for affecting a sleep disorder or mixtures thereof.

10. The method of claim 1, wherein the stimulating is effected by electrical stimulation and chemical stimulation.

11. The method of claim 1, further comprising:
   i) monitoring sleep rhythms of the brain by at least one sensor; and
   ii) providing a closed-loop feedback from the at least one sensor wherein the stimulation of the at least one nucleus is regulated.

12. The method of claim 11, wherein the at least one sensor is proximate to the cortex or subcortex of the brain.

13. The method of claim 11, wherein the at least one sensor is an internal or exterior vital sign sensor.

14. The method of claim 13, wherein the vital sign is heart rate, respiration, rapid eye movement (REM), body tone, brain activity, or combinations thereof.

15. The method of claim 14, wherein the at least one sensor detects approach of REM and the feedback loop inhibits the at least one identified nucleus.

16. The method of claim 14, wherein the at least one sensor detects approach of REM and the feedback loop activates the at least one identified nucleus.

17. The method of claim 1, wherein the at least one identified nucleus is the Locus Coeruleus.

18. The method of claim 1, wherein the at least one identified nucleus is the Dorsal Raphe Nucleus.

19. The method of claim 1, wherein the at least one identified nucleus is the posterior hypothalamus.

20. The method of claim 1, wherein the at least one identified nucleus is the Nucleus Reticularis pontis oralis.

21. The method of claim 1, wherein the at least one identified nucleus is the Nucleus Reticularis pontis caudalis.

22. The method of claim 1, wherein the at least one identified nucleus is the basal forebrain.

23. The method of claim 1, wherein the at least one identified nucleus is a Supra-Chiasmatic Nucleus of the hypothalamus.

24. The method of claim 1, wherein the sleep disorder is narcolepsy.

25. The method of claim 24, wherein the narcolepsy is manifested by the symptoms of at least one of sleep attacks, sleep paralysis, cataplexy, or hypnagogic hallucinations.

26. The method of claim 1, wherein the sleep disorder is insomnia.

27. The method of claim 1, wherein the sleep disorder is sleep apnea.

28. The method of claim 1, wherein the sleep disorder is hypersomnia.

29. The method of claim 1, wherein the sleep disorder is jet lag phenomenon.

30. The method of claim 1, wherein directly stimulating the at least one identified nucleus comprises placing an electrode on the at least one identified nucleus.

31. A method of affecting a normal awakeness-sleep cycle in a subject having an abnormal awakeness-sleep cycle said method comprising:
   a) identifying at least one nucleus in a brain of the subject, said nucleus being a nucleus of the sleep circuitry of the brain;
   b) directly stimulating the identified at least one nucleus so as to modulate the nucleus, thereby re-establishing the normal awakeness-sleep cycle in the subject, the at least one identified nucleus selected from the group consisting of the locus coeruleus, the dorsal raphe nucleus, the posterior hypothalamus, the supra-chiasmatic nucleus of the hypothalamus, the nucleus reticularis pontis oralis, the nucleus reticularis pontis caudalis, and the basal forebrain; and
   c) providing an impulse generator including an internally synchronizable clock for re-synchronizing the patient's sleep patterns, wherein the clock activates stimulation of the at least one identified nucleus to synchronize the patient's abnormal sleep patterns with a normal sleep pattern.

32. The method of claim 31, wherein the stimulating is effected by electrical stimulation.

33. The method of claim 32, wherein the electrical stimulation is performed by an electrode system.

34. The method of claim 33, wherein the electrode is implanted within the brain proximate to the at least one identified nucleus.

35. The method of claim 31, wherein the stimulating is effected by chemical stimulation.

36. The method of claim 35, wherein the chemical stimulation is performed by a pump or slow release matrix.

37. The method of claim 36, wherein the pump or slow release matrix is subcutaneously implanted in the skull of the subject, and wherein the chemical is infused proximate to the at least one identified nucleus.

38. The method of claim 37, wherein the chemical is a neurotransmitter, a neurotransmitter mimic, or an agent for affecting a sleep disorder or mixtures thereof.

39. The method of claim 31, wherein the stimulating is effected by electrical stimulation and chemical stimulation.

40. The method of claim 31, further comprising:
   i) monitoring sleep rhythms of the brain by at least one sensor; and
   ii) providing a closed-loop feedback from the at least one sensor wherein the stimulation of the at least one nucleus is regulated.

41. The method of claim 40, wherein the at least one sensor is proximate to the cortex or subcortex of the brain.

42. The method of claim 40, wherein the at least one sensor is an internal or exterior vital sign sensor.

43. The method of claim 42, wherein the vital sign is heart rate, respiration, rapid eye movement (REM), body tone, brain activity, or combinations thereof.

44. The method of claim 42, wherein the at least one sensor detects approach of REM and the feedback loop inhibits the at least one identified nucleus.

45. The method of claim 42, wherein the at least one sensor detects approach of REM and the feedback loop activates the at least one identified nucleus.

46. The method of claim 31, wherein the at least one identified nucleus is the Locus Coeruleus.

47. The method of claim 31, wherein the at least one identified nucleus is the Dorsal Raphe Nucleus.

48. The method of claim 31, wherein the at least one identified nucleus is the posterior hypothalamus.

49. The method of claim 31, wherein the at least one identified nucleus is the Nucleus Reticularis pontis oralis.

50. The method of claim 31, wherein the at least one identified nucleus is the Nucleus Reticularis pontis caudalis.

51. The method of claim 31, wherein the at least one identified nucleus is the basal forebrain.

52. The method of claim 31, wherein the at least one identified nucleus is a Supra-Chiasmatic Nucleus of the hypothalamus.

53. The method of claim 31, wherein the abnormal awakeness-sleep cycle is due to sleep deprivation.

54. The method of claim 31, wherein the abnormal awakeness-sleep cycle is due to jet lag phenomenon.

55. The method of claim 31, wherein directly stimulating the at least one identified nucleus comprises placing an electrode on the at least one identified nucleus.

* * * * *